United States Patent [19]

Husted

[11] Patent Number: 4,754,755
[45] Date of Patent: Jul. 5, 1988

[54] CATHETER WITH A ROTARY BLADE

[76] Inventor: Royce H. Husted, 711 Lakeside Dr., Wheaton, Ill. 60187

[21] Appl. No.: 77,981

[22] Filed: Jul. 27, 1987

Related U.S. Application Data

[63] Continuation of Ser. No. 874,545, Jun. 16, 1986, abandoned, which is a continuation-in-part of Ser. No. 609,846, May 14, 1984, abandoned.

[51] Int. Cl.⁴ .............................................. A61B 17/32
[52] U.S. Cl. ....................................... 128/305; 604/22
[58] Field of Search ................... 128/305, 305.1, 310, 128/751-758, 344, 348.1; 604/22

[56] References Cited

U.S. PATENT DOCUMENTS

| 1,630,239 | 5/1927 | Binkley et al. | 128/305.1 |
|---|---|---|---|
| 3,565,062 | 2/1971 | Kuris | 128/303 R |
| 3,614,953 | 10/1971 | Moss | 128/305.1 |
| 3,990,453 | 11/1976 | Douvas | 128/305 |
| 4,111,207 | 9/1978 | Seller | 128/305 |
| 4,210,146 | 7/1980 | Banko | 128/305 |
| 4,236,519 | 12/1980 | La Russa | 128/305 |
| 4,243,048 | 1/1981 | Griffin | 128/751 |
| 4,445,509 | 5/1984 | Auth | 128/305 |
| 4,493,321 | 1/1985 | Leather | 128/305 |
| 4,589,412 | 5/1986 | Kensey | 604/22 X |

FOREIGN PATENT DOCUMENTS

| 2804015 | 8/1979 | Fed. Rep. of Germany | 128/305 |
|---|---|---|---|
| 2044103 | 10/1980 | United Kingdom | 128/754 |
| 648219 | 2/1979 | U.S.S.R. | 128/755 |

Primary Examiner—Michael H. Thaler
Attorney, Agent, or Firm—Nicholas A. Camasto

[57] ABSTRACT

A catheter for inserting into a patient's artery and for remotely cutting and removing an obstruction therein, having a flexible tube equipped with a tubular blade rotatably mounted at its first end and driven by a motor through a flexible shaft, and a suction pump at its other end for cutting, ingesting and extracting the obstruction.

5 Claims, 1 Drawing Sheet

CATHETER WITH A ROTARY BLADE

This application is a continuation of application Ser. No. 874,545 filed June 16, 1986, abandoned, which is a continuation in part of application Ser. No. 06/609,846 which was filed on May 14, 1984, abandoned.

BACKGROUND AND OBJECTIVE OF THE INVENTION

With age a large portion of the population develops arterial obstructions formed by fats, fibrous material and calcified deposits, resulting in diminished blood supply to the heart, brain and other organs. Presently such obstructions are circumvented surgicly by providing a bypass or they are treated with a catheter equipped with a balloon which is inserted into the obstruction area through the arterial system and then inflated to expand the lumen through the obstruction. A problem with the balloon catheter is that it may burst the artery and in certain cases it is ineffective. Further, it does not remove the obstruction material out of the arterial system.

The object of the present invention is to provide a rotary catheter, equipped with a tubular-blade rotatably attached to its front end and driven by a flexible-shaft connected to the wall of the tubular-blade, that would cut and extract the obstruction material. This and other objects of the invention will become apparent from the foregoing discussion and the accompanying drawings.

DETAILED DESCRIPTION OF THE DRAWINGS

Figures 1, 2, 3:
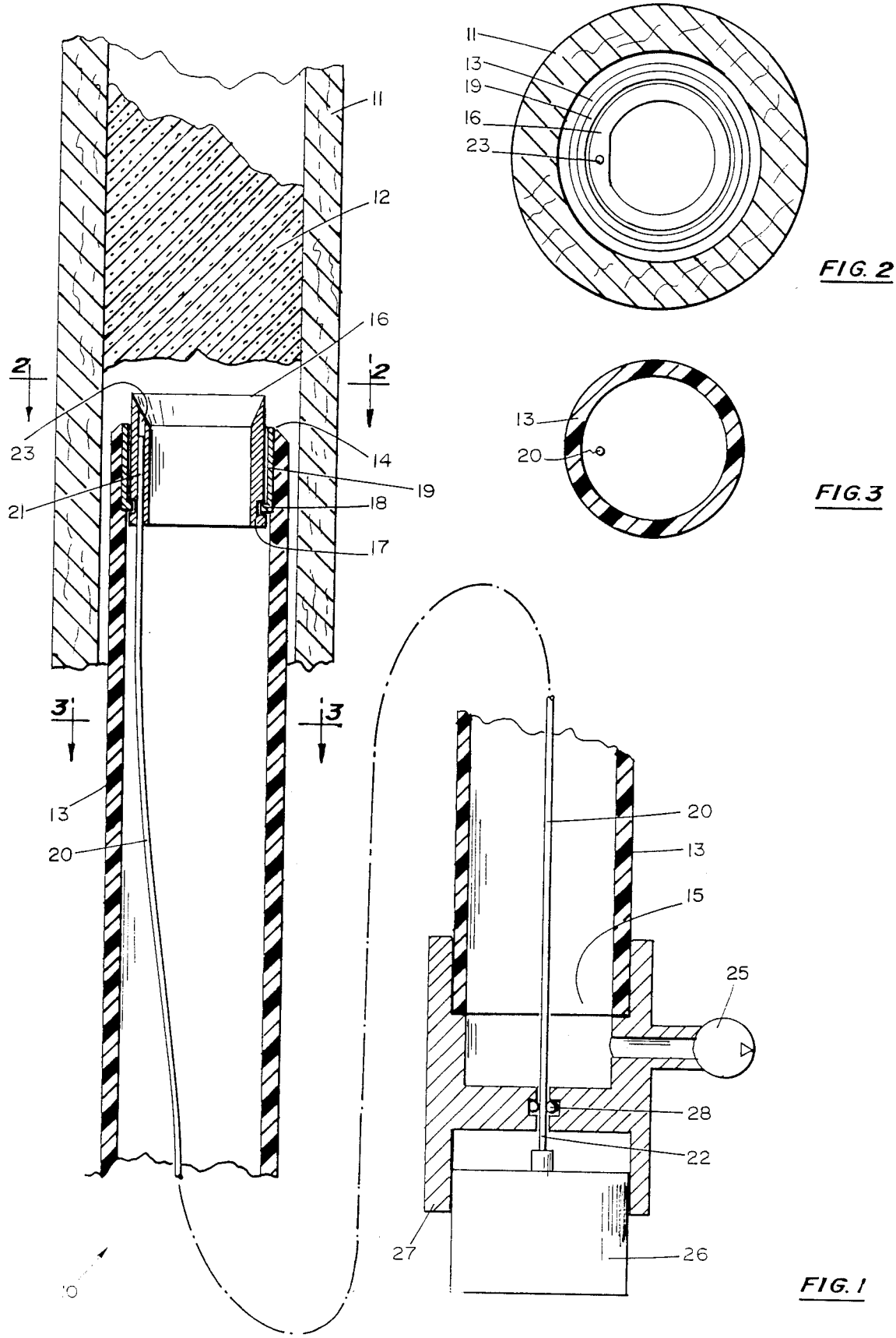
FIG. 1 shows a general cross sectional view of an embodiment of the invention.
FIG. 2 shows a cross sectional view of the embodiment along a line 2—2 marked on FIG. 1, and, FIG. 3 shows a cross sectional view of the embodiment along a line 3—3 marked on FIG. 1.

The FIGURES show a catheter 10 insertable into a patient's artery 11 for remotely cutting and removing an obstruction 12 therein, comprising:

A flexible-tube 13 having a first opening 14 and a second opening 15.

A tubular-blade 16 has a groove 17 which rides on a lip 18 of a hollow bearing 19. The hollow bearing 19 is attached to the first opening 14 and rotatably supports the tubular-blade 16.

A flexible-shaft 20, made preferably of a steel wire, having first end 21 and a second end 22, is rotatably disposed in the flexible-tube 13.

The first end 21 is coupled to the tubular-blade 16, preferably, by being inserted and affixed in a small hole 23 which is drilled in the tubular-blade's wall. This offset drive leaves the tubular blade's center open for freely accepting obstruction material, and as the material enters the flexible-tube 13 it is continuously agitated and broken down to pieces by the rotating flexible-shaft 20.

A motor (air or electric) 26 is coupled to the second end 22 for rotating the tubular-blade 16 through the flexible-shaft 20.

Suction means 25 for generating negative pressure is connected to the second opening 15, for pulling the obstruction material into and through the flexible-tube 13. The agitating action of the flexible-shaft 20 prevents the obstruction material from forming a solid obstruction in the flexible tube 13 and assists suction means in moving the obstruction material through the flexible-tube 13.

A manifold 27 is attached to the motor 26, to the flexible tube 13 and to the suction means 25. The manifold contains an O-ring seal 28 which seals around the flexible-shaft 20.

OPERATION

The process for removing an obstruction 12 from an artery 11, comprises the following steps:

Inserting into the artery 11 a first opening 14 of a catheter 10 as shown in FIG. 1, and bringing the tubular blade 16 to contact the obstruction 12, rotating the tubular-blade 16 and cutting the obstruction 12 while applying negative pressure to a second opening 15 to suck obstruction material into the catheter 10, removing the catheter 10 and its contents from the artery 11.

While the present invention has been illustrated by a single embodiment, it should be understood that various modifications and substitutions may be made without departing from the spirit of the invention or the scope of the claims.

I claim:

1. A catheter for clearing arterial obstructions comprising:

flexible tube means adapted to be inserted into an artery adjacent to an obstruction;

substantially hollow cutter means comprising a thin walled cylinder having a cutting edge at its forward end for rotatably slicing into said obstruction;

bearing means for supporting said cutter means in axial alignment with at least partially within the forward end of said flexible tube means;

a thin flexible wire means attached to the wall of said cylinder for imparting an off-center rotational drive force to said cutter means and providing a substantially obstruction-free passageway through said cylinder; and drive means for rotating said flexible wire means.

2. The catheter of claim 1 wherein said cutting edge tapers inwardly for guiding cut material from said obstruction toward the interior of said thin cylinder.

3. The catheter of claim 2, further including means for applying a negative pressure to said flexible tube means for assisting entry of cut material therein.

4. The catheter of claim 1 wherein said thin cylinder includes a hole in its wall for attachment of said wire means to said cylinder, said hole extending substantially parallel to the axis of said flexible tube means.

5. A method for clearing an obstruction in an artery comprising the steps of:

inserting into an artery a flexible tubular catheter having a hollow cutter rotatably supported therein;

positioning the tubular catheter with the hollow cutter adjacent to and in contact with an obstruction;

rotating the hollow cutter by means of an off-center flexible shaft affixed to a wall of the hollow cutter to provide a substantially obstruction free passageway into the tubular catheter for reception of cut material;

applying negative pressure to the other end of the tubular catheter to suck cut material into the catheter; and removing the catheter and its contents from the artery.

* * * * *